United States Patent [19]
Peña Garcia et al.

[11] Patent Number: 6,103,955
[45] Date of Patent: Aug. 15, 2000

[54] PROCEDURE FOR THE GENETIC TRANSFORMATION OF ADULT PLANTS OF WOODY SPECIES

[75] Inventors: Leandro Peña Garcia, Náquera; Magdalena Cervera Ocaña; José Juarez Roldan, both of Valencia; Antonio Navarro Lucas, Rocafort; Carmen Ortega Calabuig, Valencia; José Antonio Pina Lorca, Valencia; Nuria Duran Vila, Valencia; Luis Navarro Lucas, Valencia, all of Spain

[73] Assignees: Instituto Nacional De Investigacion Y Technologia Agraria Y Alimentaria (INIA); Instituto Valencia De Investigaciones Agrarias (IVIA), both of Spain

[21] Appl. No.: 09/035,469

[22] Filed: Mar. 5, 1998

[30] Foreign Application Priority Data

Mar. 5, 1997 [ES] Spain ..................................... 9700491

[51] Int. Cl.⁷ ........................... C12N 15/82; C12N 15/84; A01G 1/06; A01H 5/00
[52] U.S. Cl. ................................. 800/294; 46/6; 800/278; 800/298; 800/316; 435/430; 435/431; 435/469
[58] Field of Search .............................. 47/6, 7; 435/419, 435/468, 469, 252.2, 430, 431; 800/278, 288, 294, 298, 316

[56] References Cited

PUBLICATIONS

Cervera et al, Transgenic Research, vol. 7, pp. 51–59, 1998.
Cervera et al, Physiol. Mol. Plant Pathol., vol. 52, pp. 67–78, 1998.
Landrige et al, Plant J., vol. 2, pp. 631–638, 1992.
Mahlstede et al, Graftage, In: Plant Propagation, (J.P. Mahlstede and E. S. Haber, eds.), John Whily & Sons: New York, pp. 239–274, 1957.
Newell et al, Plant Cell Rep., vol. 10, pp. 30–34, 1991.
Hood et al, Bacteriol., vol.168, pp. 1291–1301, 1986.
Potrykus, I., Ann. Rev. Plant Physiol. Mol. Biol., vol. 42, pp. 205–225, 1991.
Pena et al, Plant Cell Rep., vol. 14, pp. 616–619, 1995.

*Primary Examiner*—David T. Fox
*Assistant Examiner*—Ashwin Mehta
*Attorney, Agent, or Firm*—Ostrolenk, Faber, Gerb & Soffen, LLP

[57] ABSTRACT

The procedure is based on the use, as vegetable starting material for the transformation, of the first shoots from the graft of buds of adult trees onto stock, the genetic transformation of explants from the adult shoots by mean of co cultivation with *Agrobacterium tumefaciens* in mother plaques, and the obtaining of complete adult woody plants by means of in vitro micrografting of the transgenic buds, apices or shoots, regenerated by means of the explants, by means of in vitro micrograft onto stock cultivated in vitro.

This procedure makes it possible to avoid the juvenile period and the high heterozygosis which affects most woody species, blossoming and fruiting of the transgenic plants are brought forward, and it permits the direct genetic transformation of commercially interesting varieties.

It has argicultural applications.

20 Claims, No Drawings

PROCEDURE FOR THE GENETIC TRANSFORMATION OF ADULT PLANTS OF WOODY SPECIES

SCOPE OF THE INVENTION

This invention refers to a procedure for the genetic transformation of adult plants of woody species, and consists both of the genetic transformation of said plants at cellular level and of the regeneration of the adult vegetable material.

BACKGROUND OF THE INVENTION

Genetic engineering applied to cultivated plants is causing a new era in agriculture. The first generation of transgenic herbaceous plants with genes of agronomic interest are already on the market and new and better perspectives are being opened for the near future. The potential of genetic improvement by means of transformation is even more interesting in the case of woody species, as most commercial varieties propagate vegetatively and are hybrids of unknown origin which basically cannot be improved by classical genetic means due to their highly heterozygotous nature. Even when traditional improvement is possible, another important obstacle is the long time period between generations. Genetic engineering permits the insertion of specific genes in the unknown genetic background of commercial varieties, adding desirable characteristics to these plants without altering other characteristics of argonomic interest.

The improvement of these woody species by means of genetic transformation will be of limited applicability unless it becomes possible to establish procedures for the genetic transformation and regeneration of adult vegetable material. Until now, procedures for the transformation of woody plants have been restricted to young tissue derived from seeds, such as, for example, zygotic embryos, cotyledons or hypocotyls (Reference 1–15). However, the sexual process completely modifies the genome of plants proceeding from seeds, altering their argonomic characteristics. In other cases in which embryogenetic cells of somatic origin, somatic embryos or vegatatively propagated tissue were used as vegetable starting material, the explants were young (Reference 3, 7, 16–33) or were rejuvanted after successive micropropagations in vitro (Reference 34–39). If these procedures and this type of vegetable starting material were used to introduce genes of agronomic interest into woody species, the regenerated transgenic plants would have juvenile qualities, and would therefore require a period of several years before it would be possible to evaluate their agronomic characteristics. Moreover, if tissue derived from seeds were used, the transformed plants would not have the same agronomic genetic characteristics as the original plants. The careful evaluation of the agronomic characteristics of adult woody species is a requirement to contemplate the commercial exploitation of new varieties in large cultivated areas.

Therefore, it is necessary to avail of a method for the genetic transformation of woody species to overcome the above mentioned problems. This aim may be obtained by means of the procedure of this invention, which consists of the direct genetic transformation of cells proceeding from adult vegetable material and the regeneration of complete adult woody plants, which permits the transformation of commercial varieties with genes of agronomic interest, and to drastically reduce the period of time necessary to evaluate the agronomic characteristics of the new varieties obtained by means of the transformation technology, thus reducing the costs and also the time period in which the new varieties arrive to the farmers and consumers.

SUMMARY OF THE INVENTION

The procedure for the genetic transformation of adult woody species of this invention is based on (i) the use, as vegetable starting material for transformation, the first shoots resulting from the grafting of tree buds onto stocks, (ii) the genetic transformation of explants proceeding from the adult buds by means of the use of a suitable vector which carries the genes which encode the characteristics of interest, such as a vector derived from *Agrobacterium tumefaciens*, non-oncogenic, and co-cultivation of the explants with said *A. tumefaciens* in feeder plates, and (iii) the obtaining of complete adult woody plants my means of the micrografting in vitro on stocks cultivated in vitro, of the transgenic buds, apices, or shoots regenerated from the explants. In the sense used in this description, the expression "genetic transformation of adult plants or woody species" includes both genetic transformation at the cellular level of the adult vegetable material and the regeneration of the transformed adult vegetable material and the obtaining of transgenic adult plants of woody species.

DETAILED DESCRIPTION OF THE INVENTION

The procedure for genetic transformation of adult plants of woody species of this invention contains the following general stages:

the inoculation of explants of adult tissue of woody species, obtained from the first shoots of the scions of buds of adult plants of woody species on stocks, with suitable vectors which carry the genes which encode the characteristics of interest, under conditions which permit the development of transgenic shoots; and the micrograft in vitro of said transgenic shoots, their buds or apices, on stocks cultivated in vitro and, subsequently, the graft of the resulting micrografted plants on other stocks which give vigour and let the taken shoots grow to generate complete adult transgenic plants, or to directly transplant the plants micrografted in vitro, to give rise to complete transgenic adult plants.

In one particular example, the vector used in the transformation of the explants derives from a non-oncogenic *Agrobacterium tumefaciens*, optionally modified to also contain the genes which encode the characteristics of interest. In this case, the procedure given by the invention consists of:

co-cultivate explants of adult tissue from woody species, proceeding from the first flushes of the grafts of buds of adult plants of woody species on stocks, such as non oncogenic *Agrobacterium tumefaciens*, optionally modified to also contain the genes which encode the characteristics of interest to be inserted into the woody plant, in feeder plates, and subsequently in a cultivation medium which favours the inducement of transgenic shoots and permits their selection;

micrograft in vitro of said transgenic shoots, their buds or apices, on stocks cultivated in vitro; and grafting of the resulting micrografted plants in vitro on other stocks which give vigour and let the taken shoots grow to generate complete adult transgenic plants.

As may be seen, the vegetable starting material used to carry out the procedure of this invention is adult tissue proceeding from the first flushes resulting from the grafts of buds of adult plants of woody species of varieties of interest which have been grafted onto stocks, preferably stocks which give vigour (vigorous stocks). The adult shoots are collected, disinfected, washed, and, under sterile conditions, are cut up to obtain explants of any type, for example of the type of segments of leaves, petioles, internodes or nodes, etc. The term first flushes as used in this description, refers to the first five flushes.

In a specific experiment, the explants obtained are genetically transformed by means of inoculation with a non-oncogenic *Agrobacterium tumefaciens* and co-culture in feeder plates over varying periods of time, from a few hours to several days. The genomic of the *A. tumefaciens* may be modified to contain the genes which encode the characteristics of interest to insert in the woody plant.

The feeder plates are prepared by pouring vegetable cellular suspensions in growing phase on a jellied culture receiver in culture receptacles. The explants are placed between both layers, liquid and gel. The feeder plates act, on the one side, as activators of the virulence region of *A. tumefaciens* and, therefore, of the transfer of genes from the cells to the explants and, on the other hand, increasing the competence of the cells of the explants to become transformed. Subsequently, the explants are cultivated in other culture media containing hormones which favour the induction of transgenic shoots from the transformed cells of the explants and a marker which permits the selection of said transgenic shoots. By means of cultivation under the appropriate light, temperature and relative humidity conditions, after a period of time of between a few weeks up to several months, the transgenic shoots are obtained. The size of these shoots varies from 1 millimeter to several centimeters.

The regenerated transgenic shoots separate from the explants and are micrografted onto in vitro cultivated stocks. The in vitro micrografted of the shoots, or of their apices or buds, may be carried out whether the stock is decapitated or not, on the inside of an incision or on the surface of the cut made during decapitation. The cotyledons of the stocks may be eliminated, and the root may be cut back. After a variable period of time, of a few weeks to several months, the in vitro micrografted plants are once more micrografted onto vigorous stocks, which may or may not be the same as those used to obtain the explants, in greenhouses, and the taken shoots grow until they give complete adult transgenic plants which, after a adequate period of time, blossom and bear fruit. The in vitro micrografted plants may also be transplanted directly into soil until they give complete adult transgenic plants.

By means of the procedure of transforming adult woody plants of this invention, it is possible to avoid the long juvenile procedure and the high heterozygosis which affect most woody species. This procedure brings forward the blossoming and fruiting of woody plants in a variable number of years depending on the species, which may be 20 years in the case of certain varieties of citrics. Moreover, this procedure permits the direct genetic transformation of commercially interesting varieties without altering their genetic and agronomic characteristics, apart from those solely and exclusively relating to the characteristic or characteristics provided by the gene or genes introduced.

As a non limiting example of the scope of this invention, the procedure developed has been evaluated for the genetic transformation of adult citric plants, specifically the Pineapple sweet orange.

EXAMPLE 1

Genetic transformation of adult Pineapple sweet orange plants.

As starting material for this example buds of adult plants from the Citric Seed Plasma Bank of the Instituto Valenciano de investigaciones Agrarias were used, which were grafted onto greenhouse cultivated Rough lemon tree.

To obtain the explants branches were cut, approximately 20 cm long, from the first three flushed after the graft. The leaves and thorns were eliminated and the branches were disinfected for 10 minutes in 2% sodium hypochlorite and washed three times with sterile water. Subsequently, transverse internode segments approximately 1 cm long were cut.

The explants obtained were genetically transformed by means of inoculation with non oncogenic *Agrobacterium tumefaciens* (Reference 26 and 27) over a period of time of between 15 and 30 minutes. Subsequently, the explants were dried on filter paper and placed in tomato feeder plates, prepared by pipetting 2–3 ml of cellular suspension of 6–7 days onto the surface of the solid culture medium with the hormones AIA (indolacetic acid), 2-iP (2-isopentenyl-adenine) and 2, 4 D (2,4 dichlorophenoxyacetic acid) on 10×1.5 cm (diameter×height) Petri dishes. Sterlie filter paper is placed between both layers. After the co culture, the explants are dried on sterile filter paper and transferred to another culture medium containing the hormone BA (6-benzilaminopurine), an inductor of the shoots and the antibiotic kanamicine, to select the transgenic shoots, and cephotaxime, to avoid contamination by *Agrobacterium*. The cultures are kept in the dark and at 26° C. over 15 days and then transferred to a 16 hour photoperiod with 45 $\mu Em^{-2}G^{-1}$ illumination, 26° C. and 60% relative humidity. The explants are subcultivated in a fresh medium every 1 weeks. After a few months transgenic shoots regenerate.

When the transgenic shoots reach a size of between 0.2 and 0.6 cm, they are separated from the explants and cut into two halves. On the bacal half analyses are carried out to verify whether the shoots are affectively transgenic. The apical half is micrografted in vitro onto Troyer citrange stock (Citrus sinensis L. Osbeck×Poncirus trifolia L. Raf.) cultivated in vitro. The Citrange Troyer plantules are decapitated leaving 1–1.5 cm of the epicotyls, the roots are cut back to 4–6 cm and the axillary cotyledons and buds are taken away. Subsequently, the regenerated buds (or their apices) are placed on the cut surface of the epicotyle, in contact with the vascular ring. After 3 weeks, the in vitro micrografted plants are grafted once more, this time in the greenhouse, onto 5 month old Rough lemon tree stock (Citrus jambhiri Lush.). After 14 months, the transgenic plants blossom and bear fruit.

BIBLIOGRAPHICAL REFERENCES

1. McGrnaha, G. H., Leslie C. A. Dandekar, A. M., Uratsu, S. L. and Yates, I. E. 1993. Transformation of pecan and regeneration of transgenic plants. *Plant Cell Rep.* 12: 634–638.

2. Mullins, M. G., Tang, F. C. A. and Facciotti, D. 1990 *Agrobacterium* mediated genetic transformation of grapevines: transgenic plants of Vitis repestris Scheele and buds of Vitis vinifers L. *Bio/Technology* 8:1041–1045.

3. Fitch, M. M. M., Manshardt, R. M., Gonzalves, D., and Slightom J. L. 1990. Stable transformation of papaya via microprojectile bomdardment. *Plant Cell Rep.* (: 189–194.

4. Hidaka, T., Omura, M., Ugaki, M., Tomiyama, M. Kato, A. A., Shshima, M., and Motoyoshi, F. 1990 *Agrobacterium*-mediated transformation and regeneration of Citrus spp. From suspension cells. *Japan. J. Breed.* 40: 199–207.

5. Mate, A., Morgens, P. H., Scorza, R., Cordts, J. M. and Callahan, A. M. 1991. *Agrobacterium*-mediated transformation of plum (Prunus domestica L.) hypocotyl slices and regeneration of transgenic plants, *Bio/Technology* 9: 853–857.

6. Smigocki, A. C. and Hammerschlag, F. A. 1991. Regeneration of plants from peach embryo cells infected with a shooty mutant strain of *Agrobacterium J. Am. Soc. Hort. Sci.* 116: 1092–1097.

7. Uematsu, C., Murase, M., Ichikawa, H., and Imamura, J. 1991. *Agrobacterium*-mediated transformation and regeneration of kiwi fruit. *Plant Cell Rep.* 10: 286–290.

8. Lamier da Cámara Machado, A., Hanzei, V., Weiss, H., Regner, F., Steinkellner, M., Mattanovich, D., Plail, R., Knapp, E., Kalthoff, B., and Katinger, H. 1992. Regeneration of transgenic plants of *Prunus armaniaca* containing the coat protein gene of plum pox virus. *Plant Cell Rep.* 11: 25–29.

9. Fitch, M. M. M., Manshardt, R. M., Gonzalves, D., Slightom, J. L. and Sanford, J. C. 1992. Virus resistant papaya plants derived from tissues bombarded with the cost protein gene of papaya ringspot virus. *Bio/Technology* 10: 1466–1472.

10. Fitch, M. M. M., Manshardt, R. M., Gonsalves, D., and Slightom, J. L. 1993. Transgenic papaya plants from *Agrobacterium*-mediated transformation of somatic embryos. *Plant Cell Rep.* 12: 245–249.

11. McGranahan, G. H., Leslie, C. A., Uratsu, S. L. and Dandekar, A. M. 1990. Improved efficiency of the walnut somatic embryo gene transfer system. *Plant Cell Rep.* 6: 512–516.

12. Dandekar, A. M., McGranahan, G. H., Vail, P. V., Uratsu, S. L., Leslie, C., and Tebbets, J. S. 1994. Low levels of expression of wild type *Bacillus thuringiensis* var. Kurstaki crylA (c) sequences in transgenic walnut somatic embryos. *Plant Sci.* 96: 151–162.

13. Scorza, R., Ravelonandro, M., Callahan, A. M., Cordts, J. M., Fuchs, M., Dunez, J., and Gonzalves, D. 1994. Transgenic plums (*Prunus domestica L.*) express the plum pox virus coat protein gene. *Plant Cell Rep.* 14: 18–22.

14. Scorza, R., Levy, L., Damsteegt, V., Yepes, L. M. Cordts, J., Hadidi, A., Slightom, J., and Gonzalves, D. 1995. Transformation of grape (*Vitis vinitera L.*) zygotic-derived somatic embryos and regeneration of transgenic plants. *Plants Cell Rep.* 14: 18–22.

15. Scorza, R., Levy, L., Damsteegt, V., Yepes, L. M. Cordts, J., Hadidi, A., Slightom, J., and Gonzalves, D. 1995. Transformation of plum with the papaya ringspot virus coat protein gene and reaction of transgenic plants to plum pox virus. *J. Am. Soc. Hort. Sci.* 120: 943–952.

16. Vardi, A., Bleichmann, S., and Aviv, D. 1990. Genetic transformation of citrus protoplasm and regeneration of transgenic plants. *Plant Sci.* 69: 199–206.

17. Rufini, E., Pellegrineschi, A., Moncuccini, M., and Mariotti, D. 1991. Increase of rooting ability in the woody species kiwi (*Actinidia deliciosa A. Chev.*) by transformation with *Agrobacterium rhizogenes* rol genes. *Plant Cell Rep.* 10: 291–295.

18. Brasileiro, A. C. M., Leple, J. C., Muzzin, J. Ounnoughi, D., Michel, M. F. and Jouanin, L. 1991. An alternative approach for gene transfer in trees using wild-type *Agrobacterium* strains. *Plant Mol. Biol.* 17: 441–452.

19. Moore, G. A., Jacono, C. C., Neidigh, J. L., Lawrence, S. D. and Cline, K. Regeneration of transgenic plants. *Plants Cell Rep.* 11: 238–2542.

20. Janssen, B. J. and Gardner, R. C. 1993. The use of transient GUS expression to develop and *Agrobacterium*-mediated gene transfer system for kiwi fruit. *Plants Cell Rep.* 13: 28–31.

21. Manders, G., Otoni, W. C., d'Utra Vaz, F. B., Blackhall, N. W., Power, J. S. and Davey, M. R. 1994. Transformation of passionfruit (*Passiflora adulis* cv flavicarpa Degener) using *Agrobacterium tumefaciens. Plants Cell Rep.* 13: 697–702.

22. Le Gall, O., Torregrosa, L., Danglot, Y., Candresse, T., and Bouquet, A. 1994. *Agrobacterium*-mediated genetic transformation of grapevine somatic embryos and regeneration of transgenic plants expressing the cost protein of grapevine chrome mosaic nepovirus (GCMV). *Plant Sci.* 102: 161–170.

23. Nakano, M., Hoshino, Y., and Mil, M. 1994. Regeneration of transgenic plants of grapevine (*Vitis vinifera L.*) via *Agrobacterium rhizogenes* mediated transformation of embryogenic calli. *J. Exp. Bot.* 45: 649–656.

24. Martinelli, L., and Mandolino, G. 1994. Genetic transformation and regeneration of transgenic plants in grapevine (*Vitis rupestris S.*) *Theor. Appl. Gen* 88: 621–620.

25. Kaneyoshi, J., Kobayshi, S., Nakamura, Y., Shigemoto, N., and Doi, Y. 1994. A simple and efficient gene transfer system of trifoliate orange. *Plant Cell Rep.* 13: 541–545.

26. Peña, L., Cervera, M., Juárez, J., Navarro, A., Pina, J. A., Durán-Vila, N., and Navarro, L. 1995. *Agrobacterium*-mediated transformation of sweet orange and regeneration of transgenic plants. *Plant Cell Rep.* 14: 616–619.

27. Pña, L., Cervera, M., Juárez, J., Navarro, A., Pina, J. A., Durán-Vila, N., and Navarro, L. 1995. High efficiency *Agrobacterium*-mediated transformation and regeneration of citrus. *Plant Sci.* 104: 183–191.

28. Mauro, M. C., Toutain S., Walker, B., Pinck, L., Otten, L., Coulos-Thevenot, P., Deloire, A., and Barbier, P. 1995. High efficiency regeneration of grapevine plants transformed with the GFLV coat protein gene. *Plant Sci.* 112: 97–106.

29. Krastanova, S., Perrin, M., Barbier, P., Demangeat, G., Cornuet, P., Bardonnet, N., Otten, L., Pinck, L., and Walter, B. 1995. Transformation of grapevine rootstocks with the coat protein gene of grapevine fanleaf nepovirus. *Plant Cell Rep.* 14: 550–554.

30. Cabrera-Ponce, J. L., Vega-Garcia, A., and Herrera-Estrella, L. 1995. Herbicide resistant transgenic papaya plants produced by an efficient particle bombardment transformation method. *Plant Cell Rep.* 15: 1–7.

31. de Cámara Machado, A., Puschmann, M., Pühringer, H., Kremer, R., Katinger, H., and Laimer da Cámara Machado, M. 1995. Somatic embryogenesis of *Prunus subhirtella* autonmo rosa and regeneration of transgenic plants after *Agrobacterium*-mediated transformation. *Plant Cell Rep.* 14: 335–340.

32. Kikkert, J. R., Hebert-Soule, D., Wallance, P. G. Striem, M. J., and Reisch, B. I. 1996. Transgenic plantlets of "Chancellor" grapevine (*Vitis sp.*) from biolistic transformation of embryogenic cell suspensions. *Plant Cell Rep.* 15: 311–316.

33. Perl, A., Lotan, O., Abu-Abied, M., and Holalnd, D. 1996. Establishment of an *Agrobacterium*-mediated transformation system for grape (*Vitis vinifera L.*). The role of antioxidants during grape-*Agrobacterium* interactions. *Nature Biotechnology.* 14: 624–628.

34. James, J. D., Passey, A. J., Barbara, D. J., and Bevan, M. 1989. Genetic transformation of apple (*Malus pumila Mill.*) using a disarmed Ti-binary vector. *Plant Cell Rep.* 7: 658–661.

35. Maheswaran, G., Welander, M., Hutchinson, J. F., Graham, M. W., and Richards, D. 1992. Transformation of apple rootstock M26 with *Agrobacterium tumefaciens*. *J. Plant Phys.* 139: 560–568.

36. Atkinson, R. G., and Gardner, R. C. 1993. Regeneration of transgenic tamarillo plants. *Plant Cell Rep.* 12: 247–351.

37. Norelli, J. L., Aldwinckle, H. S., Destéfano-Beltran, L., and Jaynes, J. M. 1994. Transgenic "Mailling 26" apple expressing the attacin E gene has increased resistance to *Erwinia amylovora*. *Euphytica* 77: 123–128.

38. Yao, J. L., Cohen, D., Atkinson, R., Richardson, K., and Morris, B 1995. Regeneration of transgenic plants from the commercial apple cultivar Royal Gala. *Plant Cell Rep.* 14: 407–412.

39. De Bont, A., Eggermont, K., Penninckx, I., Goderis, I., and Broekaert, W. F. 1996. *Agrobacterium*-mediated transformation of apple (*Malus×domestica Borkh.*): an assessment of factors affecting regeneration of transgenic plants. *Plant Cell Rep.* 15: 549–54.

We claim:

1. A procedure for the genetic transformation of citrus adult plants consisting of:
co-culturing explants of adult tissue from citrus plant species, from the first flushes of the grafts of buds of citrus adult plants onto stocks, with a non-oncogenic strain of *Agrobacterium tumefaciens,* optionally modified to further contain genes which encode the characteristics of interest to be inserted into the citrus plant, in feeder plates, and subsequently, in a culture medium which favors the induction of transgenic shoots and permits the selection thereof;
in vitro micrografting said transgenic shoots, their buds or apices, onto stocks cultivated in vitro; and
grafting the resulting in vitro micrografted plants, their buds and apices, onto other stocks which give vigor and allowing the successful grafts to grow to generate complete adult plants, or directly transplanting the in vitro micrografted plants into the soil to generate complete adult plants.

2. Procedure according to claim 1, in which said first flushes aimed at obtaining explants come from the first five shoots from the grafting of buds of adult citrus plants onto stocks.

3. Procedure according to claim 1, in which said feeder plates act to stimulate the competence of the cells of the explants for their transformation, said feeder plates containing IAA (indolacetic acid), 2iP (2-isopentenyl) and 2,4-D (2,4-dichlorophenoxyacetic acid).

4. Procedure according to claim 1, in which said culture medium which favors the induction of transgenic shoots and permits the selection thereof, contains at least one hormone which favors the induction of said transgenic shoots and markers for their selection.

5. Procedure according to claim 1, in which the adult citrus plant to be transformed in Pineapple sweet orange plant.

6. Procedure according to claim 5, in which the stock used for the in vitro micrograft is a citrange Troyer stock (citrus sinensis L. Osbeck×Poncirus trifolia L. Raf.) cultivated in vitro.

7. Procedure according to claim 5, in which the stock for the grafting of the plants micrografted in vitro is a Rough lemon tree (citrus jambhiri Lush.).

8. A procedure according to claim 2, in which the micrograft is carried out in vitro of transgenic apices, buds or shoots onto stock cultivated in vitro decapitating the stock.

9. A procedure according to claim 2, in which the micrograft is carried out in vitro of transgenic apices, buds or shoots onto stock cultivated in vitro without decapitating the stock.

10. A procedure according to claim 2, in which the cotyledons of the in vitro cultivated stock, used for in the vitro micrograft of transgenic apices, buds or shoots, are eliminated.

11. A procedure according to claim 2, in which the roots of the in vitro cultivated stock, used for the in vitro micrograft of transgenic apices, buds or shoots, are cut back.

12. A procedure according to claim 3, in which the micrograft is carried out in vitro of transgenic apices, buds or shoots onto stock cultivated in vitro decapitating the stock.

13. A procedure according to claim 3, in which the micrograft is carried out in vitro of transgenic apices, buds or shoots onto stock cultivated in vitro without decapitating the stock.

14. A procedure according to claim 3, in which the cotyledons of the in vitro cultivated stock, used for the in vitro micrograft of transgenic apices, buds or shoots, are eliminated.

15. A procedure according to claim 3, in which the roots of the in vitro cultivated stock, used for the in vitro micrograft of transgenic apices, buds or shoots, are cut back.

16. A procedure according to claim 4, in which the micrograft is carried out in vitro of transgenic apices, buds or shoots onto stock cultivated in vitro decapitating the stock.

17. A procedure according to claim 4, in which the micrograft is carried out in vitro of transgenic apices, buds or shoots onto stock cultivated in vitro without decapitating the stock.

18. A procedure according to claim 4, in which the cotyledons of the in vitro cultivated stock, used for the in vitro micrograft of transgenic apices, buds or shoots, are eliminated.

19. A procedure according to claim 4, in which the roots of the in vitro cultivated stock, used for the in vitro micrograft of transgenic apices, buds or shoots, are cut back.

20. The procedure of claim 4, wherein said hormone is benzylaminopurine.

* * * * *

UNITED STATES PATENT AND TRADEMARK OFFICE
CERTIFICATE OF CORRECTION

PATENT NO. : 6,103,955
DATED      : August 15, 2000
INVENTOR(S): Leando Pena Garcia et al.

It is certified that error appears in the above-identified patent and that said Letters Patent is hereby corrected as shown below: Title page, item

[73] INSTITUTO NACIONAL DE INVESTIGACIOÑ Y TECNOLOGIA AGRARIA Y ALIMENTARIA (INIA); INSTITUTO VALENCIANO DE INVESTIGACIO'NES AGRARIAS (IVIA), both of Spain Signed and Sealed this First Day of May, 2001

*Attest:*

NICHOLAS P. GODICI

*Attesting Officer*   Acting Director of the United States Patent and Trademark Office